United States Patent [19]

Franco

[11] 4,184,498

[45] Jan. 22, 1980

[54] SANITARY NAPKIN

[76] Inventor: Pierre Franco, Plateau St. Jean, Rascas 81, Castres, France

[21] Appl. No.: 785,908

[22] Filed: Apr. 8, 1977

[30] Foreign Application Priority Data

Jun. 14, 1976 [FR] France .............................. 76 17963

[51] Int. Cl.² .......................................... A61F 13/16
[52] U.S. Cl. ................................. 128/290 R; 128/284
[58] Field of Search ............... 128/287, 284, 290, 296, 128/285, 286

[56] References Cited

U.S. PATENT DOCUMENTS

| | | | |
|---|---|---|---|
| 2,566,451 | 9/1951 | Julien | 128/290 R |
| 2,683,458 | 7/1954 | Cunningham | 128/290 R |
| 2,928,394 | 3/1960 | Roberts | 128/290 R X |
| 3,371,667 | 3/1968 | Morse | 128/290 R |
| 3,805,790 | 4/1974 | Kaczmarzyk et al. | 128/290 R |

Primary Examiner—Stephen C. Pellegrino
Attorney, Agent, or Firm—Pollock, Vande Sande & Priddy

[57] ABSTRACT

Disposable sanitary napkin comprising an absorbent structure imprisoned between an outer, impermeable film and an inner, permeable covering, by the edges of the film and the edges of the covering being joined together. Said absorbent structure comprises a main absorbent pad having the form of an oblong, tapering towards the rear, and having two side swellings and possibly a secondary absorbent pad less compact than the main absorbent pad. The invention also relates to a method of manufacturing such a sanitary napkin.

11 Claims, 5 Drawing Figures

SANITARY NAPKIN

BACKGROUND OF THE INVENTION

The present invention relates to a disposable sanitary napkin and to a method of manufacturing same.

SUMMARY OF THE PRIOR ART

Different types of sanitary napkins, also called sanitary towels, are already known which comprise an absorbent structure.

These sanitary napkins are made in more or less elaborate designs to improve the holding in place and efficacy of this absorbent structure.

In the most elaborated sanitary napkins, the absorbent structure is imprisoned between an outer, impermeable film and an inner permeable covering, the edges of said film and said covering being joined together. These sanitary napkins are generally rectangular in form and exist in different sizes and thicknesses.

Small, thin sanitary napkins are produced with a view to avoiding local discomfort to the wearer, and for aesthetic purposes, to be concealed as much as possible.

However, these sanitary napkins have certain drawbacks due essentially to the fact that the absorption and protection that they confer are proportional to their size and thickness.

Moreover, presently existing sanitary napkins are uncomfortable and do not prevent the skin and clothes from being stained. Therefore, as soon as the absorbent structure begins to become wet, the feeling of discomfort is evident and persists until the napkin is changed.

On the other hand, the absorption of the presently existing sanitary napkins is not uniform over the whole surface of the absorbent structure and the top surface is locally rapidly saturated, thus causing discomfort and the inevitable staining.

Furthermore, the holding of these sanitary napkins in place by means of adhesive elements or any other suitable system does not prevent said napkins from moving, this increasing the discomfort and possibilities of soiling. This is essentially due to the fact that the inner surface of these sanitary napkins is flat and does not follow the shape of the anatomy.

It is an object of the invention to provide a novel sanitary napkins which avoids the above-mentioned drawbacks.

SUMMARY OF THE INVENTION

The invention therefore has for an object a sanitary napkin whose inner surface is of such anatomical shape as to assure holding in place and maximum comfort for the whole time that it is used. This anatomical shape enables a sanitary napkin of reduced dimensions and with maximum efficacy to be produced.

The invention also has for its object a sanitary napkin enabling a larger quantity of menstrual flow to be absorbed and avoiding humidity being retained on the surface.

The sanitary napkin according to the invention comprises, in known manner, an absorbent structure imprisoned between an outer, impermeable film and an inner, permeable covering by the edges of the film and the edges of the covering being joined together and is characterised in that said absorbent structure comprises a main absorbent pad which is formed by compacting an absorbent material, which is oblong in shape, tapering towards the rear, and which has two side swellings projecting on the inner covering side, joining at the front and rear of the napkin and connected together by a thinner central portion whose density of compaction is higher than said side swellings.

In a preferred embodiment of the present invention, said absorbent structure further comprises a secondary absorbent pad imprisoned between the main absorbent pad and the inner covering.

DESCRIPTION OF THE PREFERRED EMBODIMENTS

Figure 1:
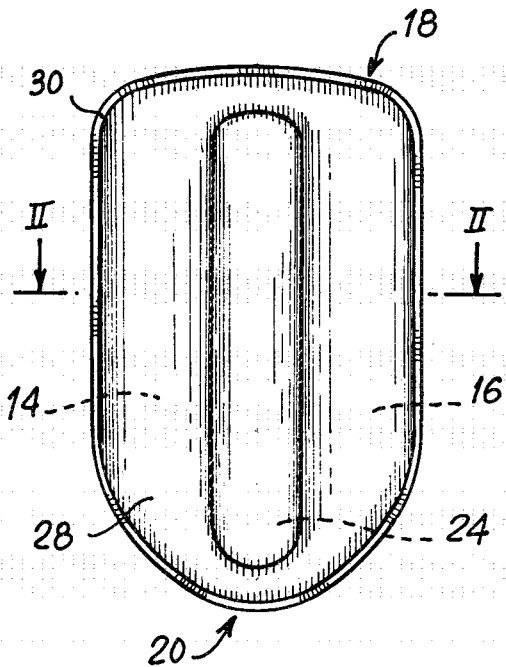
FIG. 1 is a plan view of a sanitary napkin according to the invention, showing the inner covering.
Figure 2:
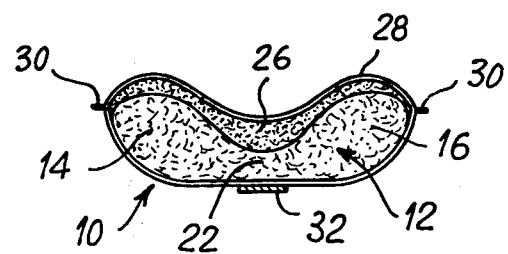
FIG. 2 is a section through II—II of FIG. 1.
Figure 3:
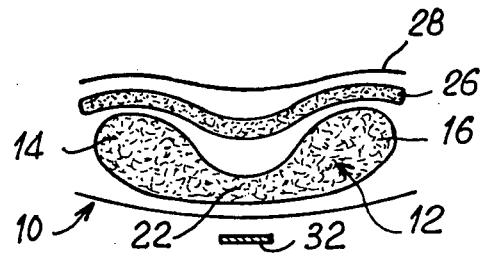
FIG. 3 is an exploded view of the section of FIG. 2.

FIGS. 1 to 3 show a sanitary napkin which comprises an outer, impermeable film 10, made for example of plastic material, on which is superposed a main absorbent pad 12, whose shape corresponds to the anatomy, of compact structure allowing an absorption of menstrual flow in two side swellings 14 and 16 adapted to expand while acting as receptacle. These two side swellings 14 and 16 join at the front 18 of the napkin, i.e., at the end of the napkin adapted to be applied on the pubis, and at the rear 20 of the napkin (see. FIG. 1). These two swellings are also connected together by a thinner portion 22 of absorbent material, which thus defines a central elongated portion 24, which is less thick and of a compaction density higher than the side swellings 14 and 16. These two swellings make it possible to give the sanitary napkin the desired anatomical shape for comfort and good retention during its use.

On the main absorbent pad 12 is superposed a secondary absorbent pad 26 less compact than the main absorbent pad 12, which acts as transfer means towards the main absorbent pad.

On the secondary absorbent pad 26 is superposed an inner permeable covering 28 which comes into contact with the skin. This covering 28, made for example of a material of nonwoven type, will preferably be hydrophobic in order to allow the transfer of the menstrual flow towards the absorbent pads, without being impregnated itself.

The main absorbent pad 12 and the secondary absorbent pad 26 are imprisoned between the outer film 10 and the inner covering 28 by the edges of the film 10 and the edges of the covering 28 being joined over the whole peripheral zone 30 of the napkin (see. FIGS. 1 and 2).

This joining may be effected for example by adhesion, heat-welding or by mechanical crimping of the edges.

To improve the holding of the sanitary napkin in place during use, the film 10 is provided on its outer surface with at least one double-face adhesive element 32 comprising a removable protective film which, once removed, enables the napkin to be fitted and securely positioned in the wearer's briefs or panties.

The sanitary napkin according to the invention may preferably be ovoid, as shown in FIG. 1, the wider part being the front part adapted to be applied on the pubis.

The dimensions of the sanitary napkin of the invention may be reduced, while ensuring good protection. For example, the napkin may be 90 mm long and from 50 to 55 mm wide.

The superposition of two absorbent pads of different compaction densities allows an absorption in the most compact absorbent pad, i.e., the main absorbent pad, the less compact absorbent pad, i.e., the secondary absorbent pad, acting as transfer means. In fact, the menstrual flow will tend to pass through the secondary absorbent pad and be absorbed in the main absorbent pad with higher absorbent power, this enabling the surface of the napkin, which is in contact with the skin, to remain dry as long as possible.

This main absorbent pad may have different textures, obtained by compacting sheets, flocks or fibers of an absorbent material so as to obtain a sufficient density to make a semirigid shell having the ovoid form described hereinabove, and having two side swellings joined together by a thinner portion of absorbent pad.

The main absorbent pad 12 may be constituted by compacted cellulosic cotton wool flocks or sheets. However, in a preferred embodiment, the main absorbent pad 12 is constituted by a mixture of viscose and cotton fibers, the proportion of which may vary as a function of the desired rate of absorption. It is possible, for example, to obtain a mixture of 62.5% cotton and 37.5% viscose, using five sheets of cotton and three sheets of viscose.

The shape of the main absorbent pad which, in section, is in the form of an open U (see. FIG. 2), allows a perfect positioning of the napkin which affords good protection. Apart from this advantage of comfort and security, the central, thinner part 24, which is of higher density of compaction, acts as transfer means with the result that the menstrual flow absorbed therein passes into the side swellings of the napkin. The main absorbent pad will be saturated from the bottom of the napkin upwards and from the side swellings to the center.

The secondary absorbent pad 26 is of lower density of compaction than the main absorbent pad and may be made of a less absorbent material than the main absorbent pad. This secondary absorbent pad may be constituted by a sheet or fibers, projected or strewn at random, of an absorbent material such as cellulosic cotton wool.

Figure 4:
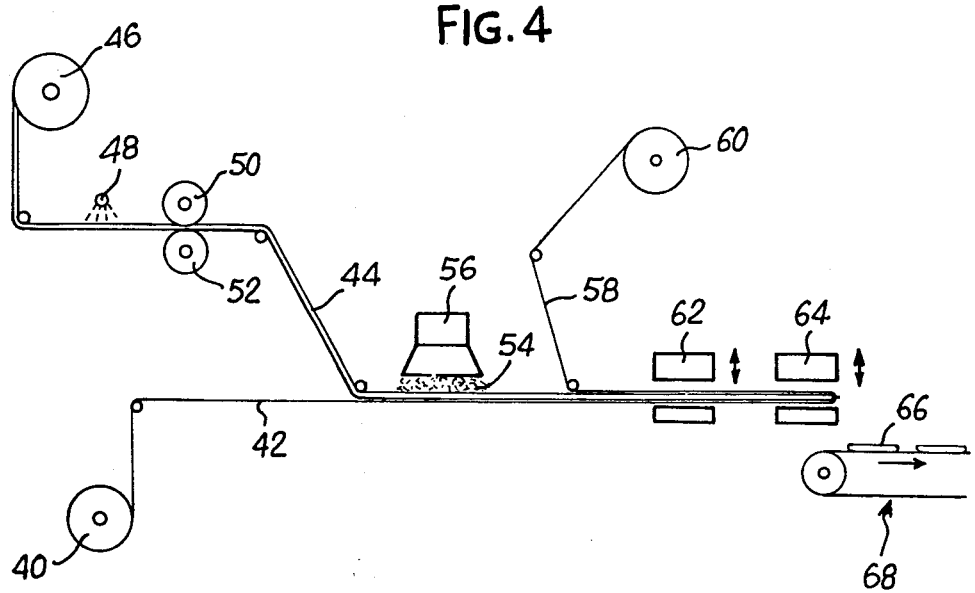
FIG. 4 schematically illustrates a machine for manufacturing sanitary napkins according to the invention.

FIG. 4 schematically shows a machine for carrying out the method of manufacturing sanitary napkins according to the invention.

This machine comprises a reel 40 from which is continuously unwound an impermeable sheet 42 which is to constitute the outer film of the napkins. There is superposed on the sheet 42 an absorbent layer 44 which is to constitute the main absorbent pad of the napkins. This absorbent layer is unwound from a reel 46, humidified by means of a water-spray pipe 48 and preformed by means of a calendering roller 50 associated with a roller 52, so as to form a succession of impressions each corresponding to the ovoid shape described hereinabove.

After superposition of the absorbent pad 44 on the sheet 42, a secondary absorbent layer is superposed on the absorbent pad 44, which is to constitute the secondary absorbent pad of the napkins. In the embodiment shown in FIG. 4, this secondary absorbent layer is obtained by random projection or strewing of fibers 54 of an absorbent material by means of a suitable device 56.

A permeable sheet 58 which is to constitute the inner covering of the napkin is unwound from a reel 60 and superposed on the assembly of sheets and layers already formed.

The assembly of the four superposed elements passes through a heat-welding station 62 adapted to join the edges of the sheet 58 and the edges of the sheet 42, along a contour corresponding to that of the napkin, imprisoning therebetween the preformed main absorbent pad and the secondary absorbent pad associated therewith.

After the heat-welding stage, the assembly passes to a cut-out station 64 which cuts it into unitary elements, such as 66, which are evacuated for example by means of a conveyor belt 68 and thereafter packed.

Figure 5:
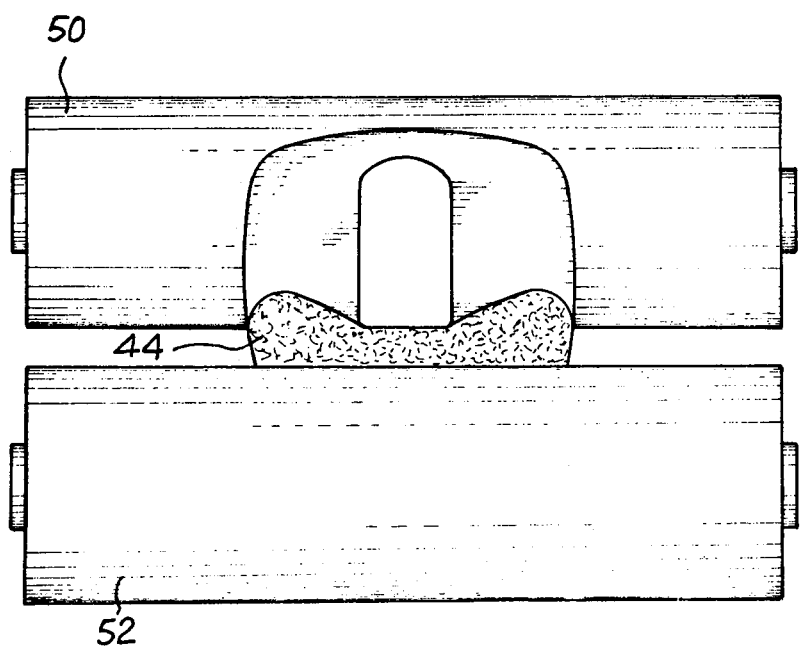
FIG. 5 shows a calendering roller, intended for preforming the main absorbent pad of the sanitary napkin according to the present invention.

FIG. 5 shows the calendering roller 50 and the roller 52 associated therewith, for preforming the main absorbent layer 44 of the napkins.

It will be appreciated that the machine shown in FIG. 4 may undergo certain modifications. Thus, in the case of the sanitary napkins according to the invention comprising only one absorbent pad, namely the main absorbent pad, the device 56 will be eliminated from the machine of FIG. 4.

On the other hand, if it is desired to make sanitary napkins also comprising a secondary absorbent pad, the device 56 may be replaced by a reel for unwinding a strip of secondary absorbent material.

The preformed main absorbent pads may be cut out before being superposed on sheet 42.

The edges of the impermeable film and the edges of the covering may be joined together by adhesion or by mechanical crimping.

Cutting out may be effected by means of a punch or a cut-out roll, either after or at the same time as the joining stage.

What is claimed is:

1. A disposable sanitary napkin comprising an absorbent structure, an outer, impermeable film and an inner, permeable covering, said absorbent structure comprising a main absorbent pad which is formed by compacting an absorbent material to impart to it a generally oblong shape having front and rear ends, two side swellings projecting on the inner covering side, joining at the front and rear of the napkin and connected together by a thinner central portion whose density of compaction is higher than that of said side swellings, said main absorbent pad having in section the form of an open U conferring anatomical shape to the napkin and allowing the menstrual flow absorbed in the thinner central portion to pass into the side swellings.

2. A sanitary napkin according to claim 1, wherein said main absorbent pad is formed by compacting an absorbent material in sheet form.

3. A sanitary napkin according to claim 1, wherein said main absorbent pad is formed by compacting absorbent material in the form of flocks.

4. A sanitary napkin according to claim 1, wherein said main absorbent pad is formed by compacting absorbent material in fiber form.

5. A sanitary napkin according to claim 2 or 3, wherein the said absorbent material comprises cellulosic cotton wool.

6. A sanitary napkin according to claim 1, in which the main absorbent pad is formed by compacting sheets of cotton and sheets of rayon.

7. A sanitary napkin according to claim 1, in which the outer film is provided on its outer surface with at least one double-face adhesive element provided with a removable protective film.

8. A sanitary napkin according to claim 1, in which the absorbent structure further comprises a secondary absorbent pad imprisoned between the main absorbent pad and the inner covering.

9. A sanitary napkin according to claim 8, in which the secondary absorbent pad comprises a sheet of an absorbent material.

10. A sanitary napkin according to claim 1, in which the secondary absorbent pad is less compact than the main absorbent pad.

11. A sanitary napkin according to claim 8, wherein the said absorbent material comprises random fibers of absorbent material.

* * * * *